United States Patent [19]
Suzuki et al.

[11] Patent Number: 6,020,325
[45] Date of Patent: Feb. 1, 2000

[54] METHOD FOR INHIBITING REPLICATION OF HIV

[75] Inventors: Fujio Suzuki; Hidetaka Sasaki; Makiko Kobayashi, all of Galveston, Tex.

[73] Assignees: Zeria Pharmaceutical Co., Ltd.; Natsu Maruyama, both of Tokyo, Japan

[21] Appl. No.: 09/264,686

[22] Filed: Mar. 9, 1999

[51] Int. Cl.[7] .......................... A61K 31/715; A61K 31/70
[52] U.S. Cl. ................................. 514/54; 514/44
[58] Field of Search ..................... 536/1.1, 22.1, 536/124; 514/45, 49, 44, 50, 54, 269; 435/101, 134; 424/92

[56] References Cited

U.S. PATENT DOCUMENTS

| | | | |
|---|---|---|---|
| 4,746,511 | 5/1988 | Kobatake et al. | 424/92 |
| 5,521,161 | 5/1996 | Malley et al. | 514/45 |

FOREIGN PATENT DOCUMENTS

| | | | |
|---|---|---|---|
| 9520673 | 8/1995 | France | . |

OTHER PUBLICATIONS

Arp et al., "Expression and Immunogenicity of the Entire Human T Cell Leukemia Virus Type I Envelope Protein Produced in a Baculovirus System," *Journal of General Virology*, 74(2), 211–222 (1993).

Okunade et al., "Antimicrobial Properties of Alkaloids from *Xanthorhize Simplicissima*," *Journal of Pharmaceutical Sciences*, 83(2), 404–406 (Mar. 1994).

Guleria et al., "Auxotropic Vaccines for Tuberculosis," *Nature Medicine* (*New York*), 2(3), 334–337 (1996).

Ishihara et al., "Phase II Clinical Trial of MY–1 For Adult T Cell Leukemia," *Skin Cancer*, 10(2), 257–270 (1995); only Abstract provided.

Bernier et al., "Mycobacterium Tuberculosis Mannose- -Capped Lipoarabinomannan Can Induce NR–kappaB–Dependent Activation of Human Immunodeficiency Virus Type 1 Long Terminal Repeat in T Cells," *J. General Virology*, 79(pt.6), 1353–1361 (Jun., 1998).

"Diagnostics—Mycobacterium Avium," *AIDS Weekly*, Issue of Nov. 28, 1994, only 349 word abstract provided, page location(s) not available.

Vila et al., "Absence of Viral Rebound After Treatment of HIV–Infected Patients with Didanosine and Hydroxycarbamide," *The Lancet*, 350, 635–636 (Aug. 30, 1997).

*Primary Examiner*—L. Eric Crane
*Attorney, Agent, or Firm*—Oblon, Spivak, McClelland, Maier & Neustadt, P.C.

[57] ABSTRACT

A method for inhibiting replication of HIV, which comprises subjecting HIV-infected cells to a composition (a) comprising as a primary component a polysaccharide derived from a hot aqueous solvent extract of tubercle bacillus.

13 Claims, 1 Drawing Sheet

Replication of HIV in cultures of PBMCs treated with composition (a)

METHOD FOR INHIBITING REPLICATION OF HIV

BACKGROUND OF THE INVENTION

1. Field of the Invention:

The present invention relates to a method for the inhibition of HIV (human immunodeficiency virus) replication.

2. Discussion of the Background

AIDS is a disease caused by an HIV infection, and the number of patients suffering from this disease has markedly increased in recent years. The therapy for AIDS has involved use of nucleoside-type anti-HIV agents, such as Zidovudine (Azidothymidine, AZT) and Didanosine (ddI).

Unfortunately, these conventional anti-HIV agents do not provide a sufficient therapeutic effect. Consequently, development of a new anti-HIV agent which exhibits an enhanced, and thus adequate, therapeutic effect is required.

More recently, the present inventors discovered and have described in U.S. Ser. No. 09/038,041, that the therapeutic effect of nucleoside-type anti-HIV agents on AIDS patients may be improved by the combined use of a hot water extract of human tubercle bacillus and the agents. This composition was found to reduce the mortality of mice with AIDS as compared to the anti-HIV agent being administered alone.

However, a need for a simple and effective therapeutic agent for inhibiting the replication of HIV continues to exist.

SUMMARY OF THE INVENTION

Accordingly, it is an object of the present invention to provide a simple and effective agent affording a sufficient therapeutic effect for inhibiting replication of HIV. This method will entail subjecting HIV-infected cells to a composition containing as a primary component a polysaccharide derived from a hot aqueous solvent extract of tubercle bacillus.

It is also an object of the present invention to provide an anti-HIV agent, which contains the above-mentioned composition as an active ingredient.

Yet another object of the present invention is to provide an anti-HIV composition containing the above-mentioned composition.

The above objects and others are provided by a method for inhibiting replication of HIV, which entails subjecting HIV-infected cells to a composition containing as a primary component a polysaccharide obtained from a hot aqueous solvent extract of tubercle bacillus.

BRIEF DESCRIPTION OF DRAWINGS

The drawing illustrates the anti-HIV effect of the composition of the present invention on the replication of HIV in cultures.

DETAILED DESCRIPTION OF THE PREFERRED EMBODIMENTS

Figure 1:
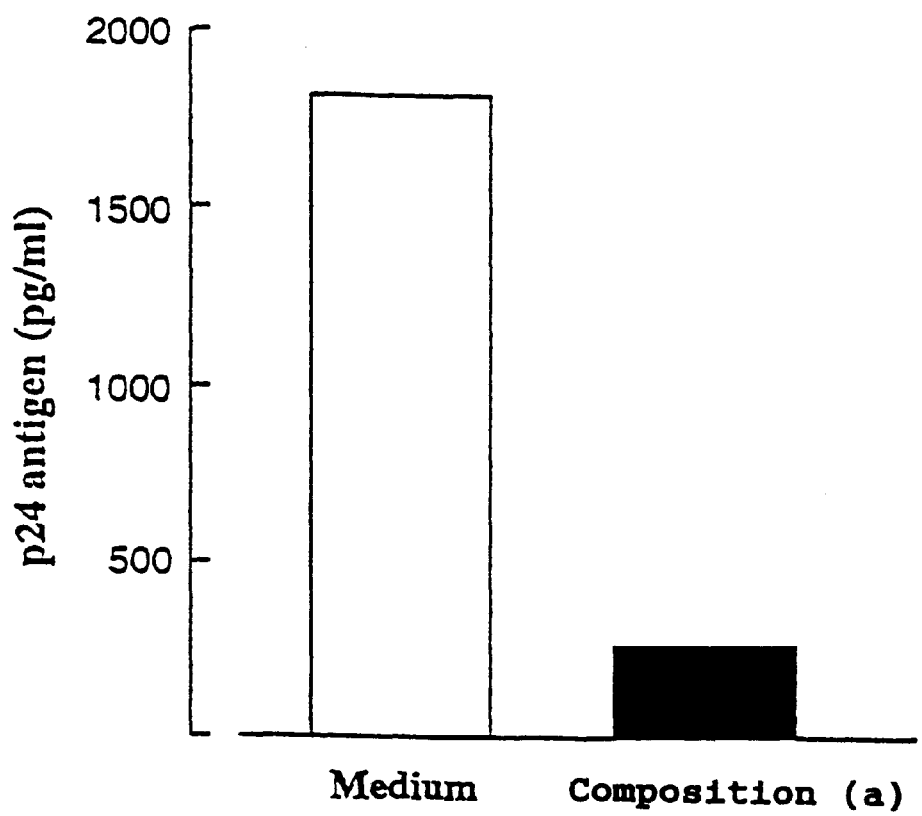

The present invention is predicated upon the surprising discovery that a hot aqueous solvent extract of tubercle bacillus, by itself, exhibits an anti-HIV effect. Although hot aqueous solvent extract of tubercle bacillus was previously known to promote recovery of white blood cells by increasing the count thereof after radiotherapy treatments, such a use would clearly not have suggested the surprising new use afforded by the present invention.

In more detail, the composition which is used in the present invention; i.e., a composition containing as its primary component a polysaccharide derived from a hot aqueous solvent extract of tubercle bacillus, has previously shown to recover the white blood cell count that was reduced by radiotherapy for cancers (see, among others, "The Clinical Report (Basic and Clinical Report)," 24(4), 1973(199) and "*Nippon Igaku Hoshasen Gakkai Zasshi,*" 50(8) , 993 (1990)).

However, the effect of the present composition, i.e., hot aqueous solvent extract of tubercle bacillus, on HIV was unknown prior to the present invention.

The present composition herein designated "(a)" contains a polysaccharide as its primary component. Preferably, composition (a) contains a polysaccharide whose primary constituents are arabinose, mannose and glucose, as well as a small amount of nucleic acid. Preferably, the polysaccharide has a molecular weight ranging from about $5\times10^2$ to $5\times10^4$ as measured by the gel filtration method. The nucleic acid content of composition (a) is preferably about 0.05–0.3 wt. %. The composition (a) may contain about 1–5 wt. % the protein. Preferably, the mannose content of the polysaccharide is about 10–72 wt. %, the arabinose content about 3–30 wt. %, and the glucose content about 5–30 wt. %. The composition (a) of particular preference has the mannose content about 40–50 wt. %, the arabinose content about 15–25 wt. %, and the glucose content about 5–15 wt. %.

Composition (a) is obtained by purifying a hot-aqueous solvent extract of tubercle bacillus. More specifically, composition (a) is obtained by subjecting cells of tubercle bacillus to extraction with hot aqueous solvent. The extract is then subjected to protein removal treatment and to treatment for removing polysaccharides of molecular weight of about $10^5$ or more. The tubercle bacillus may be selected from both types of human Mycobacteria and non-human Mycobacteria, but human Mycobacteria are preferred. Examples of non-human Mycobacteria include *Mycobacterium bovis, Mycobacterium avium, Mycobacterium microti, Mycobacterium kansasii, Mycobacterium marium* and *Mycobacterium intracellulae*. Examples of human Mycobacteria include Aoyama B, H37Rv and H37Ra with Aoyama B being particularly preferred. The extraction with hot aqueous solvent is more accurately performed with aqueous solvent of a temperature of about 80° C. to 120° C. Examples of aqueous solvent include fresh water, saline, sea water and sodium hydroxide solution with fresh water being preferred. The protein removal treatment is more thoroughly performed by causing proteins to precipitate by use of a protein precipitant such as sulfosalicyclic acid, trichloroacetic acid, or phosphotungstic acid, followed by the subsequent collection of the supernatant. The treatment to remove polysaccharides at a molecular weight of $10^5$ or more, is preferably performed by causing polysaccharides or high molecular weight to precipitate by use of ethanol, methanol, or acetone in a suitable amount, followed by the subsequent collection of the supernatant.

In accordance with the present invention, composition (a) may be directly applied to HIV-infected cells so as to act on the cells. Composition (a) is preferably present in an amount of approximately 1–1000 μg/ml, with a more particular presence of 5–500 μg/ml, in the in vitro system. Also composition (a) is preferably administered by injection with a preference of a subcutaneous injection, in the in vivo case.

As calculated in terms of the saccharide content of arabinose in the in vivo case, the dose of composition (a) is preferably about 2–200 pg per day, more preferably about 20–100 μg per day.

When composition (a) is administered to a subject in need thereof, it is preferably prepared in the form of pharmaceutical compositions suitable for the aforementioned administration routes by incorporating thereto a generally employed, pharmaceutically acceptable carrier. Examples of carriers useful for the preparation of pharmaceutical compositions include; vehicles, binders, lubricants, disintegrants, coating agents, emulsifiers, suspensions, solvents, stabilizers, absorption aids, water for injection use, and tonicity agents.

Reference to certain examples, which are provided solely for purposes of illustration and which are not intended to be limitative, will now be used to further describe the present invention.

REFERENTIAL EXAMPLE 1

(Preparation of Composition (a))

*Mycobacterium tuberculosis* strain Aoyama B, which had been lyophilized and stored at −20° C., was subjected to seed culture at 37±1° C. in a Sauton-potato medium[(1)]. The resultant cells were inoculated to a production medium[(2)] and incubated for 5–7 weeks at 37±1° C. Next, the harvested cells were washed with fresh water for injection use, followed by fresh water for injection use being added to the wet cells, at an amount 20 times the weight of the wet cells. To thereby obtain an extract, the mixture was heated to 100° C. for 120 minutes. The extract was filtered by use of a 0.45 μm-membrane filter and concentrated under reduced pressure so that the saccharide content (converted to D-arabinose by the phenol-sulfuric acid method) fell within the range of 4.0–6.0 mg/ml, to thereby obtain a concentrate. Subsequently, in order to remove proteins, 1%(w/v) sulfosalicylic acid was added to the concentrate. The mixture was allowed to stand for 15–20 minutes at a temperature no higher than 10° C. Precipitates were removed by centrifugal separation (at a temperature of 10° C. or lower, 1,150×g, 10 minutes), to thereby recover the supernatant. The protein concentration of the supernatant was not more than 0.30 mg/ml (Lowry method, calculated as tyrosine). The supernatant was further processed to remove sulfosalicylic acid until the content of sulfosalicylic acid fell below the detection threshold (10 ppm or less, calorimetric method using ferric chloride solution). To have the saccharide content fall within the range of 1.8–2.2 mg/ml, the resultant solution was concentrated under reduced pressure. The concentrate was then combined with sodium chloride (0.9% (w/v)) and cold ethanol having a volume equal to that of the concentrate. The mixture was allowed to stand for no less than 40 hours at a temperature no higher than 10° C., then the precipitated polysaccharides of high molecular weight were removed by centrifugal separation (at a temperature of 10° C. or lower, 2,040×g, 10 minutes). Subsequently, the supernatant was combined with four times the volume of cold ethanol, and the mixture was allowed to stand for no less than 40 hours at a temperature no higher than 10° C., to thereby recover precipitates. The precipitates were dissolved in water for injection use, and after the saccharide content was adjusted to 1.8–2.2 mg/ml, the solution was subjected to filtration by use of a 0.45 μm membrane filter and to sterilization in an autoclave (121° C., 20 minutes), to thereby prepare a composition (a) solution.

(1) Sauton-potato medium

Washed potato slices were soaked in a Sauton medium, followed by sterilization for 15 minutes at 115° C. The resultant material was used as a Sauton-potato medium.

| Sauton Medium | |
|---|---|
| L-asparagine (monohydrate) | 4.0 g |
| Citric acid (monohydrate) | 2.0 g |
| Magnesium sulfate (heptahydrate) | 0.5 g |
| Potassium monohydrogenphosphate (anhydrate) | 0.5 g |
| Ammonium iron citrate | 0.05 g |
| Glycerol | 60 ml |

The ingredients above were dissolved in water to make a total volume of 1,000 ml. By use of sodium hydroxide solution, the pH was adjusted to 7.0–7.3.

| (2) Production medium | |
|---|---|
| L-asparagine (monohydrate) | 4.0 g |
| Citric acid (monohydrate) | 2.0 g |
| Magnesium sulfate (heptahydrate) | 0.5 g |
| Potassium monohydrogenphosphate (anhydrate) | 0.5 g |
| Ammonium iron citrate | 0.05 g |
| Glycerol | 60 ml |

The ingredients above were dissolved in water to make a total volume of 1,000 ml, followed by sterilization in an autoclave (121° C., 20 minutes). By use of sodium hydroxide solution, the pH was adjusted to 7.0–7.3.

The physicochemical properties of the composition (a) solution were as follows.

(1) Appearance: Pale yellow clear liquid (2) pH: 4.50–5.30

(3) Protein content: 3.5 wt. % (as an amino acid, in a freeze-dried product)

(4) Nucleic acid content: 0.1 wt. % (in a freeze-dried product)

(5) Constituent monosaccharides of polysaccharide:

Mannose 43.4 wt. %,

Arabinose 18.2 wt. %, and

Glucose 10.4 wt. %.

Methods for determining the constituent monosaccharides of polysaccharide:

The polysaccharide was hydrolyzed with 2N trifluoroacetic acid for 2 hours at 100° C., and then subjected to liquid chromatography making use of 2-cyanoacetamide fluorescein derivative (S. Honda, et al., Anal. Chem., 52, 1079 (1980)).

TEST EXAMPLE 1

HIV-1 IIIB (0.01 M.O.I.) was subjected to a two-hour absorption by peripheral blood mononuclear cells (PBMCs, $2\times10^6$ cells/ml, derived from a seronegative donor) activated with phytohemagglutinin (PHA), to thereby prepare HIV-infected PBMCs. The HIV-infected PBMCs were cultured in the RPMI-1640 medium supplemented with 20% FCS and 20 U/ml of IL-2 at 37° C. in the presence of composition (a). Seven days after the infection, HIV-1 p24 antigens present in the culture fluids were quantified by ELISA.

As is apparent from the results shown in FIG. 1, the addition of a 100 μg/ml dose of composition (a) reduces the amount of HIV-1 p24 antigens, proving that the composition provides an anti-HIV effect.

As may readily be seen, the present invention provides a surprising ability to inhibit replication of HIV.

Having described the present invention, it will now be apparent to one of ordinary skill in the art that many changes and modifications may be made to the above-described embodiments without departing from the spirit and the scope of the present invention.

What is claimed is:

1. A method of inhibiting the replication of HIV, comprising administering to a patient in need thereof an effective amount of composition comprising a polysaccharide produced by a hot aqueous solvent extraction of tubercle bacillus, wherein the polysaccharide is comprised of arabinose, mannose and glucose residues.

2. The method of claim 1, wherein the composition further comprises nucleic acid produced by the hot aqueous solvent extract of tubercle bacillus.

3. The method of claim 1, wherein the polysaccharide has a molecular weight of about $5 \times 10^2$–$5 \times 10^4$, as determined by gel filtration.

4. The method of claim 1, wherein the tubercle bacillus is a human tubercle bacillus.

5. The method of claim 1, wherein the human tubercle bacillus is an Aoyama B strain.

6. The method of claim 1, wherein the hot aqueous solvent extraction is conducted at a temperature of about 80° C. to 120° C.

7. The method of claim 1, wherein the composition further about 1 to 5 wt. % of protein.

8. The method of claim 2, wherein the composition further contains about 1 to 5 wt. % of protein.

9. The method of claim 1, wherein the polysaccharide is comprised of 10–72 wt. % mannose, 3–30 wt. % of arabinose and 5–30% wt. % of glucose.

10. The method of claim 1, wherein the polysaccharide is comprised of 10–72 wt. % mannose, 3–30 wt. % of arabinose and 5–30% wt. % of glucose.

11. The method of claim 1, wherein the aqueous solvent is fresh water, saline, sea water, or sodium hydroxide solution.

12. The method of claim 1, wherein the aqueous solvent is fresh water.

13. The method of claim 1, wherein the composition is obtained by a process comprising:

(a) extracting tubercle bacillus cells with an aqueous solvent at a temperature of at least about 80° C., to obtain a concentrate which comprises protein and polysaccharide;

(b) precipitating protein in the concentrate from (a), to produce a precipitate and a supernatant comprising polysaccharide; and (c) precipitating polysaccharide in the supernatant from (b); and (d) isolating the precipitated polysaccharide from (c), followed by dissolving the precipitated polysaccharide in water.

* * * * *

UNITED STATES PATENT AND TRADEMARK OFFICE
CERTIFICATE OF CORRECTION

PATENT NO.   : 6,020,325
DATED        : February 1, 2000
INVENTOR(S)  : Fujio Suzuki, et al.

It is certified that error appears in the above-identified patent and that said Letters Patent is hereby corrected as shown below:

<u>Column 5,</u>
Line 26, "about 1 to 5 wt.% of protein." should read -- contains about 1 to 5 wt.% of protein. --.

Signed and Sealed this

Sixteenth Day of October, 2001

Attest:

*Attesting Officer*

NICHOLAS P. GODICI
*Acting Director of the United States Patent and Trademark Office*